United States Patent [19]

Pollard

[11] Patent Number: 4,608,982

[45] Date of Patent: Sep. 2, 1986

[54] FORCEPS

[76] Inventor: Clifford W. Pollard, 106 Anzac Ave., Redcliffe, Queensland, Australia, 4020

[21] Appl. No.: 749,816

[22] Filed: Jun. 28, 1985

[30] Foreign Application Priority Data

Mar. 7, 1984 [AU] Australia ............................. PG5810

[51] Int. Cl.[4] ............................................ A61B 17/28
[52] U.S. Cl. .................................. 128/321; 128/303 R
[58] Field of Search .................... 128/321, 303 R, 346

[56] References Cited

U.S. PATENT DOCUMENTS

| 1,761,761 | 6/1930 | Vicente | 128/303 R |
| 2,305,156 | 12/1942 | Grubel | 128/321 |
| 3,143,114 | 8/1964 | McCarthy et al. | 128/303 R |
| 3,844,274 | 10/1974 | Nordstrom | 128/321 |
| 4,300,564 | 11/1981 | Furihata | 128/321 |
| 4,484,911 | 11/1984 | Berlin et al. | 128/346 |

Primary Examiner—Robert Peshock
Assistant Examiner—C. W. Shedd
Attorney, Agent, or Firm—Larson and Taylor

[57] ABSTRACT

Surgical forceps for use and association with a catheter for gaining access to a body cavity so as to release fluid therefrom. The forceps include handle means which preferably are finger loops attached to a pair of elongate members pivotally attached to each other at a common intersection point. There also is provided a pair of opposed gripping or cutting jaws which substantially are located at adjacent ends of the pair of elongate members which are each remote from the finger loops. There is also provided at least a partially tubular retaining passage to facilitate the insertion therefrom and retention therein of a catheter or catheter support. Preferably the retaining passage comprises opposed projections on each elongate member adjacent a respective gripping jaw which are channel like in shape so that when the forceps are in at least a partially closed position the retaining passage is formed.

3 Claims, 9 Drawing Figures

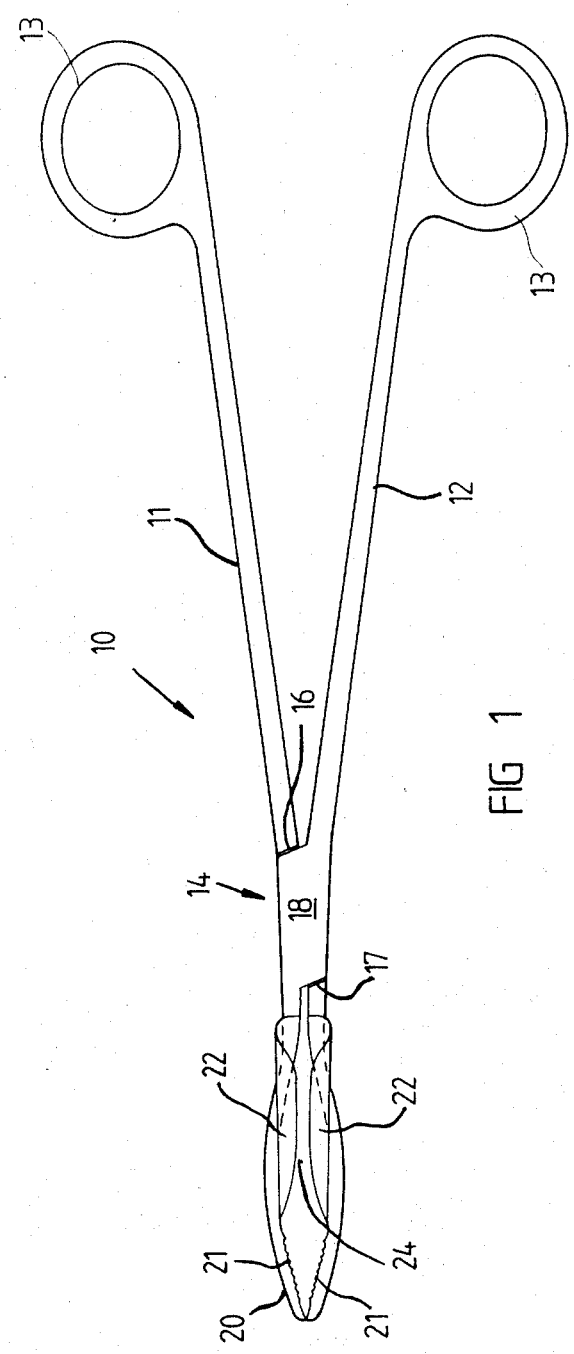
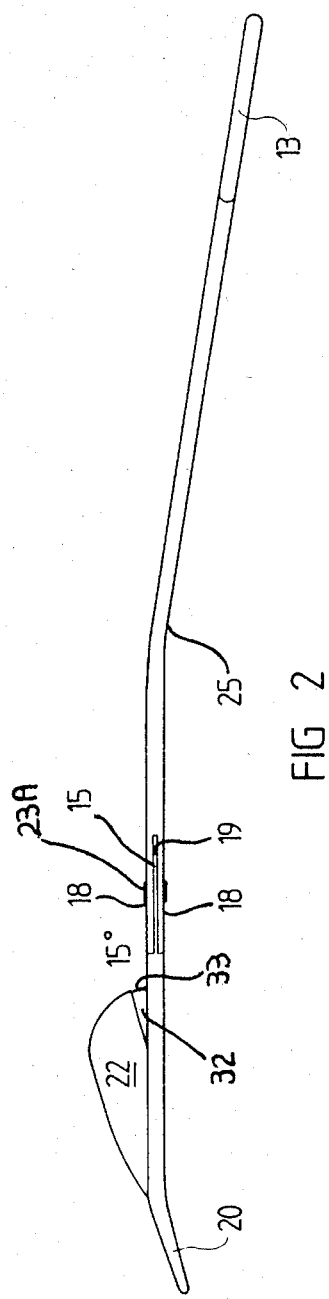
FIG 1
FIG 2

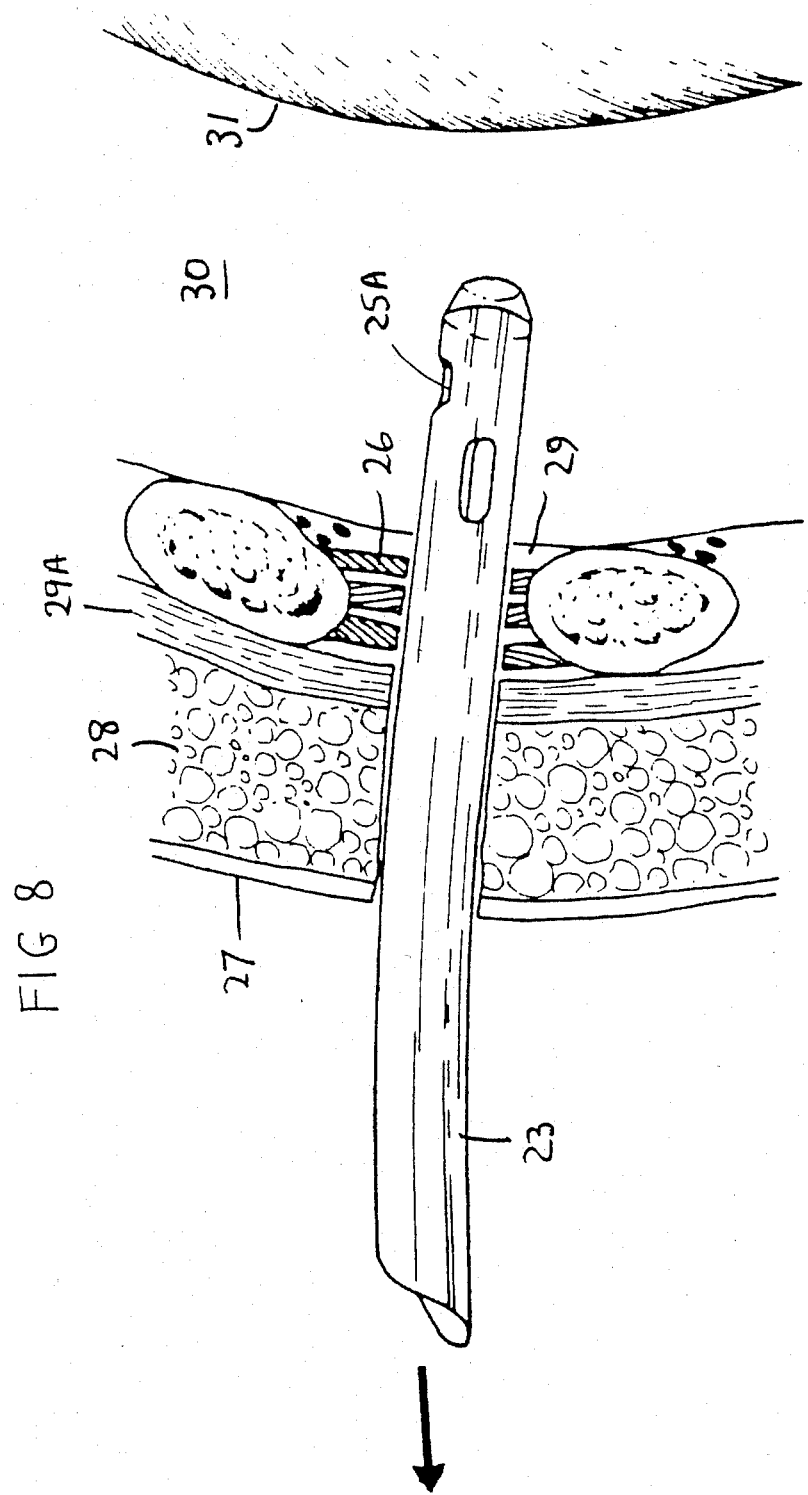

FORCEPS

This invention relates to improved forceps particularly for use in association with a catheter for opening up the pleural cavity and other body cavities so as to release fluid such as air and/or blood contained therein.

Hitherto in relation to surgical procedures for opening up of body cavities and in particular the pleural cavity it was necessary to carry out the sequential steps of incising initial layers of skin and fat with a scalpel until muscle layers were exposed and subsequently blunt dissect with conventional forceps through the muscle layers until the pleural cavity or pleural lining was reached and thereafter insert a catheter through the surgical path created.

While this procedure was found to be satisfactory in some cases it was found that disadvantages of this procedure involved frequent repetition of the blunt dissecting step because of the fact that often the initial track or path created by the first dissection through the muscle layers was lost due to relaxation of the tissues after withdrawal of the forceps. It was then necessary to perform a further dissection with subsequent loss of surgical speed and operational time.

In another conventional procedure it was common practice to excise the initial layers of skin and fat and then force the catheter and its supporting trocar or support through the exposed muscle layer until the pleural cavity was reached. This procedure was also disadvantageous because the forcing procedure with the trocar often penetrated too far into the pleural cavity and subsequently contacted the lung or blood vessels which included veins and arteries and in particular the intercostal artery. Also it was considered that this procedure was somewhat crude or primitive and caused unnecessary damage to the muscle layers.

Conventional forceps that have been utilized in the abovenamed prior art procedures have comprised a pair of elongate members pivotally attached to each other at a common intersection point thereby providing one set of mutually adjacent ends having finger loops and another set of mutually adjacent ends providing gripping jaws wherein each gripping jaw is provided with a plurality of gripping ribs on a respective inner surface thereof. While such forceps were useful for blunt dissection of muscle tissue as described above they have no role to play after this task was completed and it was necessary to subsequently insert the catheter through the gap or path in the muscle layers created by the forceps.

It therefore is an object of the invention to provide forceps that are useful in the abovementioned surgical procedures in such a manner that when used in association with a catheter that the problems of the prior art may be alleviated.

It is also another object of the invention to provide a surgical procedure using the forceps of the invention that also alleviate the problems of the conventional surgical procedures described above.

The forceps of the invention include handle means and a pair of opposed gripping or cutting means suitable for dissection through muscle tissue. The principal characteristic of such forceps is that adjacent said pair of gripping or cutting means there is provided a retaining passage which may be at least partly tubular to facilitate the insertion therethrough and retention therein of a catheter or catheter support.

In one embodiment the forceps of the invention may be provided with elongate members pivotally attached to each other at a common intersection point thereby providing one set of mutually adjacent ends having finger loops which constitutes an appropriate handle means and another set of mutually adjacent ends wherein each end provides a gripping or cutting jaw. In this arrangement said another set of mutually adjacent ends may be provided with opposed inner surfaces or gripping surfaces of a corrugated or serrated nature or alternatively may have a plurality of gripping ribs.

Preferably the intersection point is located nearer the gripping jaws than the finger loops in this particular embodiment. The pivotal attachment means utilized for attachment of the elongate members may be of any suitable type such as a pivot pin. There also may be associated therewith joint means which may be similar to a conventional pair of scissors wherein in the closed position mating edges of each elongate member abut. More preferably the joint means comprises a box joint wherein one elongate member is provided with a flattened or generally planar blade or web having opposed recesses which is interposed between mutually opposed planar parts of the other elongate member. The arrangement may be such that in an opened out position the blade or web of said one elongate member extends at an angle to the planar parts of the other elongate member and in the closed position the opposed planar parts of the other elongate member are accommodated within the confines of each recess of the blade or web of said one elongate member.

The retaining passage is suitably channel like or tubular in configuration and in one form may comprise a projection of at least part tubular configuration on one elongate member adjacent said gripping jaw. More preferably however there are provided opposed projections on each elongate member adjacent their respective gripping jaws which are each arcuate or channel like in shape so that when the forceps are in the closed position a retaining passage of at least part tubular shape is formed through which a catheter or catheter support may be inserted.

A catheter tube is used for insertion into canals, vessels, passageways or body cavities so as to permit injection or withdrawal of fluids or substances or to maintain the openness of an existing passageway. In one form it may comprise a plastics tube formed from transparent material suitably having measurements or other identifying indicia marked thereon. One end may be open so as to receive a catheter support or trocar which is a sharp pointed instrument which may be used to pierce a body cavity and be withdrawn leaving the catheter in place so as to serve as a drainage outlet. The other end of the plastics tube may be provided with slots or apertures to permit fluid from the body cavity to gain access to the interior of the catheter tube.

In regard to the present invention the forceps of the invention may be utilized to blunt dissect through a muscle layer after initial excision of fat and skin and the forceps then maintained in position while the catheter may be inserted through the aforesaid retaining passage and thus gain access to the body cavity so as to permit the drainage of blood and/or air or other fluid therefrom when required.

It will also be appreciated that the opposed cutting means associated with the forceps of the invention may comprise scissor blades if desired but it is preferred that opposing gripping jaws as described above are utilized as they are more suitable for dissection through muscle tissue.

Reference may now be made to a preferred embodiment of the invention as shown in the attached drawings wherein:

FIG. 1 is a rear perspective view of a pair of forceps constructed in accordance with the present invention;

FIG. 2 is a front perspective view of the forceps shown in FIG. 1;

FIG. 8 is a schematic view showing the next step in the surgical technique of the invention wherein the forceps are removed and the catheter is connected to an underwater drain.

Figures 3, 3A:
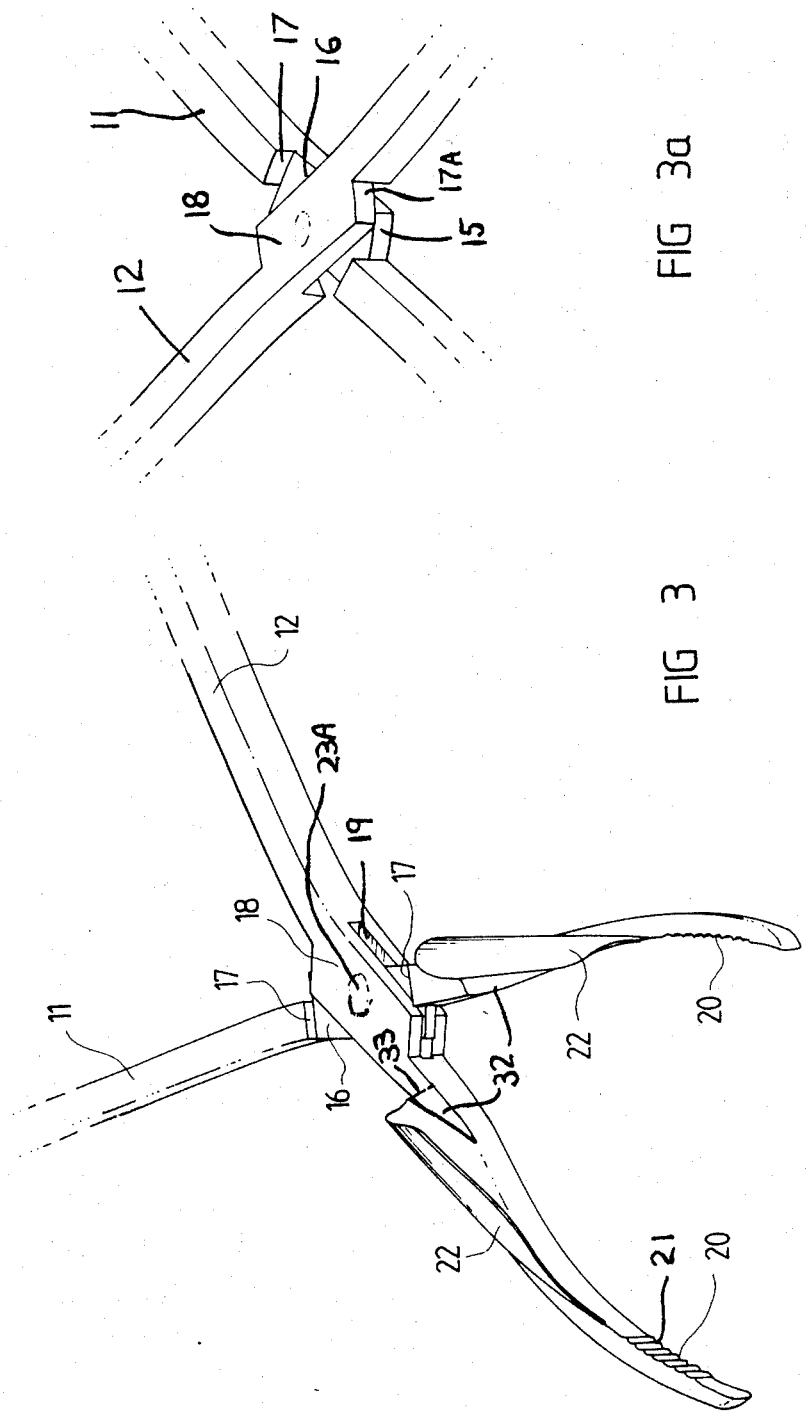
FIG. 3 is a perspective view of the forceps of FIG. 1 in the opened out position.
FIG. 3a is a detailed perspective view of the box joint.

The forceps 10 as shown in FIGS. 1-3 comprise a pair of elongate members 11 and 12 each having a finger loop 13 at one end thereof in the same manner as a pair of conventional scissors. There is also shown pivotal attachment means 14 between each member 11 and 12 in the form of a box joint wherein one member 11 is provided with a generally flattened web 15 having opposed recesses 16 each having peripheral edges 17 and the other member 12 is provided with opposed planar parts 18 having a slot 19 interposed therebetween. In the closed position each planar part 18 is received within recess 16 and bears against edges 17. In this embodiment edges 17A of planar portions 18 bear against edges 17 of recesses 16.

There is also shown gripping jaws 20 having gripping ribs or corrugations 21. There is also provided upstanding projections 22 adjacent jaws 20 which are arcuate as shown so that when the forceps 10 are in the closed position a retaining passage 24 may be formed for a catheter 23. There is also shown pivot pin 23A.

Each member 11 and 12 is preferably offset at 25 so as to provide access for catheter 23 in the surgical procedure shown in FIGS. 4-8.

Figure 4:
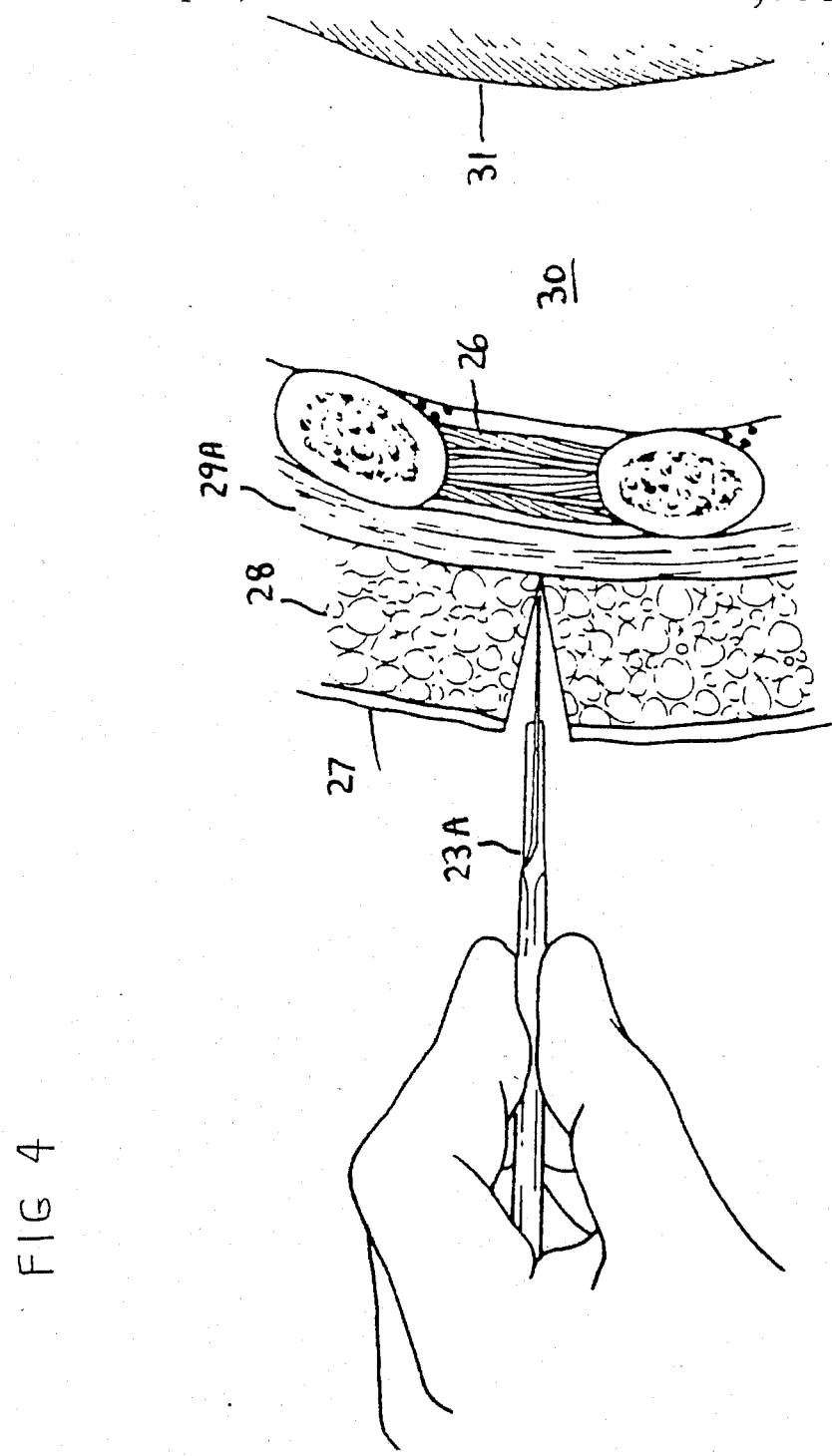
FIG. 4 is a schematic view of an initial incision being made through skin and subcutaneous tissue to the fascia over the muscle covering the pleural cavity.
Figure 5:
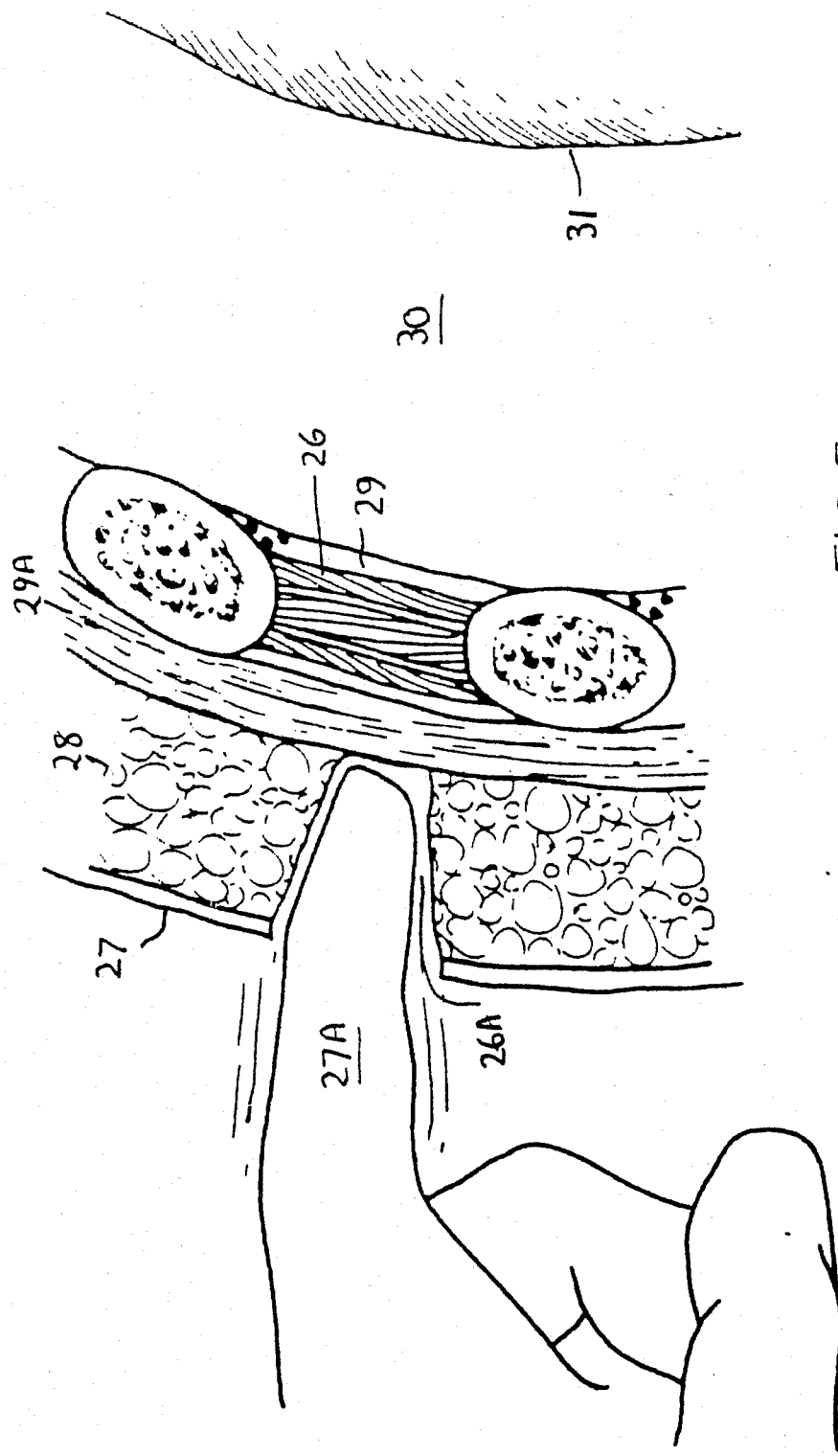
FIG. 5 is a schematic view palpating the intercostal space.

In FIG. 4 the first stage of a surgical operation using the forceps of the invention is shown where a scalpel 23A is used to make an initial incision through skin 27 and fat or subcutaneous tissue 28 to fascia 29A overlying muscle layer 26. In FIG. 5 the intercostal space 26A is then palpated by finger 27A.

Figure 6:
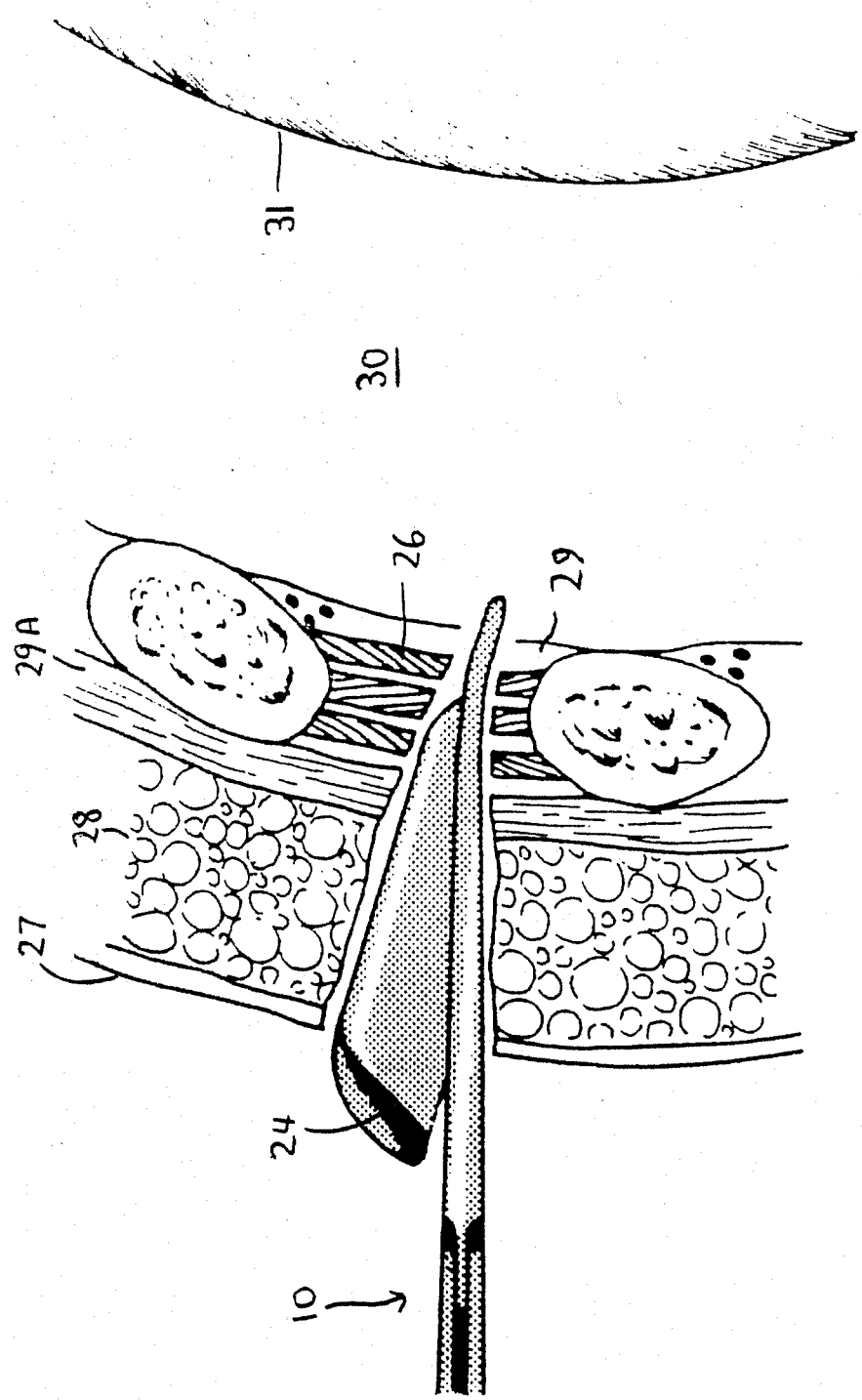
FIG. 6 is a schematic view showing blunt dissection of the forceps of FIG. 1 through muscle layers until the pleural cavity is entered.

In FIG. 6 the forceps 10 are used to blunt dissect through muscle layer 26 after the initial incision is made through skin 27 and tissue 28 as shown in FIG. 4. After a cut is made through the pleura 29 the pleural cavity 30 is then exposed as well as lungs 31.

Figure 7:
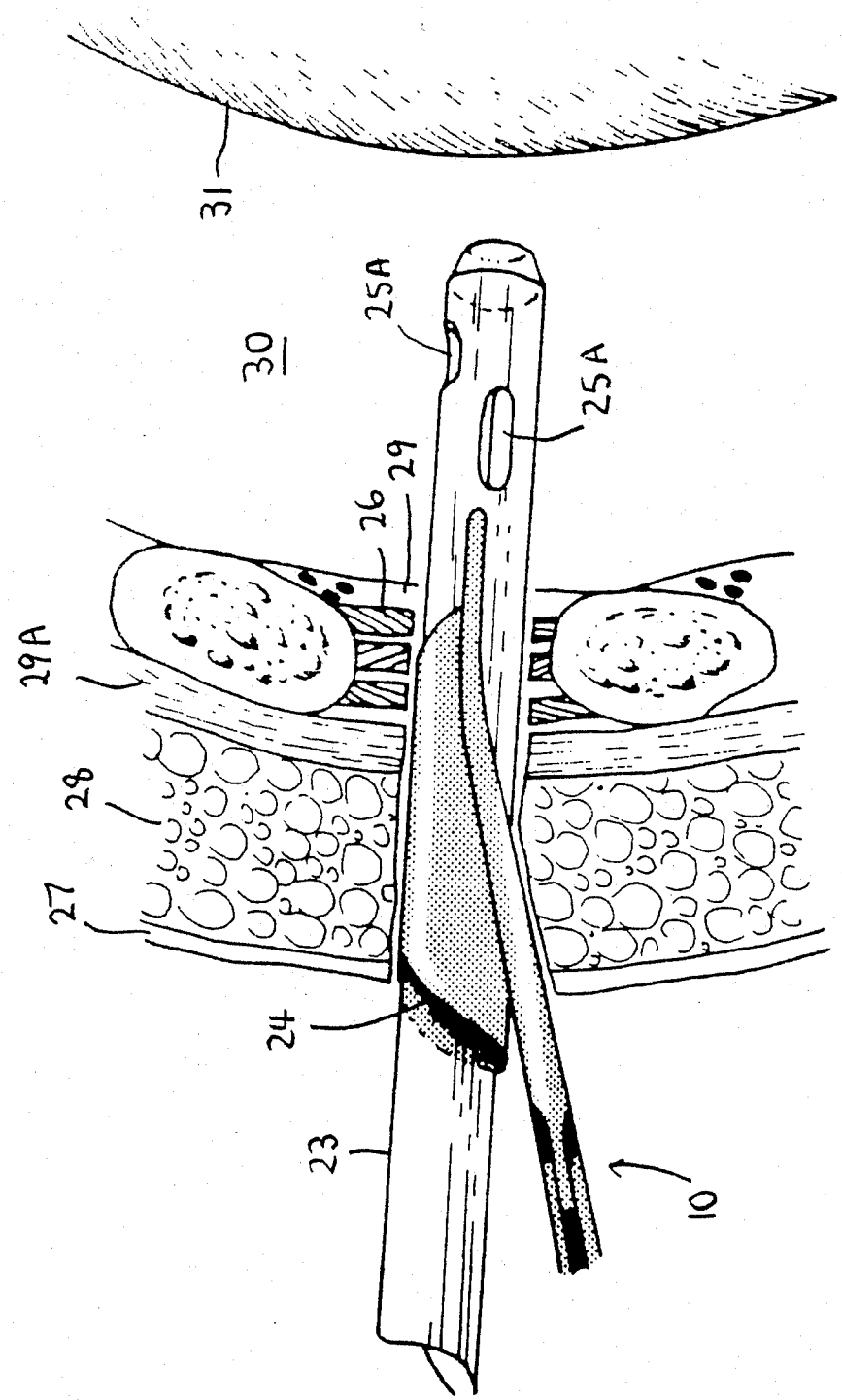
FIG. 7 is a schematic view of the forceps of FIG. 1 used for supporting the insertion of a catheter through into the pleural cavity.

In FIG. 7 the forceps 10 are then opened slightly and an intercostal catheter 23 inserted through retaining passage 24. Catheter 23 has apertures 25A in its inner end so as to provide access from the pleural cavity 30. The forceps are then removed and the catheter connected to an underwater drain (not shown) shown by the arrow in FIG. 8.

It will also be appreciated that the forceps of the invention may be used for exposing the peritoneal cavity after blunt dissecting through the abdominal wall muscles in a similar manner as shown in FIGS. 4-8.

The projections 22 may be provided with a slot 32 as shown in FIG. 2 or may have the slot 32 omitted as shown by dotted line 33.

I claim:

1. Surgical forceps for use in association with a catheter for gaining access to a body cavity so as to drain fluid therefrom, said forceps including:

(i) a pair of elongate members pivotally attached to each other at a common intersection point thereby providing one set of mutually adjacent ends comprising finger loops and another set of mutually adjacent ends comprising a pair of opposed blunt dissection jaws for flunt dissection of tissue blocking access to said body cavity, said blunt dissection jaws each having a free end and said free ends abutting in an operational position thereof to facilitate said blunt dissection of said tissue; said common intersection point being located nearer the blunt dissection jaws than said finger loops and said elongate members forming said blunt dissection jaws initially diverging from each other adjacent the common intersection point and subsequently converging to form said free ends; and (ii) a retaining passage formed by opposed channel shaped projections on each elongate member, each channel shaped projection being spaced from and located rearwardly of the free end of the blunt dissection jaw of the associated elongate member and projecting outwardly from the plane of the blunt dissection jaws.

2. Surgical forceps as claimed in claim 1 wherein said dissection jaws are provided with opposed inner surfaces of a corrugated nature to thereby define a plurality of gripping ribs.

3. Surgical forceps as claimed in claim 1 comprising pivotal attachment means for said pair of elongate members comprising a box joint wherein one elongate member is provided with a web having opposed recesses which is interposed between mutually opposed planar parts of the other elongate member whereby in use in an opened out position the web of said one elongate member extends at an angle to the planar parts of the other elongate member and in the closed position the opposed planar parts of the other elongate member are accommodated within the confines of each recess of the web.

* * * * *